(12) United States Patent
Jederström

(10) Patent No.: US 6,180,601 B1
(45) Date of Patent: *Jan. 30, 2001

(54) LOW MOLECULAR WEIGHT HYALURONIC ACID WITH PEPTIDE OR PROTEIN

(75) Inventor: Gustaf Jederström, Stockholm (SE)

(73) Assignee: Pharmacia AB, Stockholm (SE)

(*) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/666,497

(22) PCT Filed: Jan. 10, 1995

(86) PCT No.: PCT/SE95/00011

§ 371 Date: Jun. 18, 1996

§ 102(e) Date: Jun. 18, 1996

(87) PCT Pub. No.: WO95/18635

PCT Pub. Date: Jul. 13, 1995

(30) Foreign Application Priority Data

Jan. 10, 1994 (SE) .................................................. 9400036

(51) Int. Cl.[7] .......................... A61K 38/00; A61K 38/02; C07K 5/00; C07K 7/00
(52) U.S. Cl. ................... 514/12; 514/2; 514/21; 514/54; 514/412; 514/420; 514/576; 514/777; 536/55.1; 424/78.05
(58) Field of Search .................... 514/2, 12, 21, 514/54, 420, 576, 777, 912; 536/55.1; 424/78.05; 530/356; 435/244

(56) References Cited

U.S. PATENT DOCUMENTS 4,641,120 * 2/1987 Nevo et al. .......................... 435/244
4,703,108 * 10/1987 Silver et al. .......................... 530/356
5,166,331 * 11/1992 della Valle et al. .................... 514/54

FOREIGN PATENT DOCUMENTS 0 193 510 * 9/1986 (EP).
2235204 * 2/1991 (GB).

OTHER PUBLICATIONS

Dijke, "Growth Factors for Wound Healing" Bio/Technology, v.7 (Aug., 1989), pp. 793–798.*

Maelson et al., "Shaped Article" CAPLUS #1986: 628, 859.*

* cited by examiner

Primary Examiner—Avis M. Davenport
(74) Attorney, Agent, or Firm—Dinsmore & Shohl LLP

(57) ABSTRACT

The invention relates to freeze-dried soft, flexible and continuous matrix of low-molecular weight hyaluronic acid or salt thereof, in which the molecular weight of the hyaluronic acid is preferably between 50 000 and 200 000 Da, containing at least one peptide or protein. It also relates to a pharmaceutical composition in the form of a layer which is characterised by this freeze-dried low-molecular weight hyaluronic acid containing at least one peptide or protein. The drug is preferably chosen from at least one of GH, IGF-I, IGF-II and/or EGF and could be mixtured with an antibiotic agent. The process for the manufacture of this matrix and the use of the pharmaceutical composition for the manufacturing of a drug for wound healing is claimed. The invention discloses a method for accurately obtaining a predetermined dosage of a topically administerable drug which is characterised by freeze-drying a water solution of low-molecular weight hyaluronic acid and the peptide or protein to form a layer.

21 Claims, No Drawings

LOW MOLECULAR WEIGHT HYALURONIC ACID WITH PEPTIDE OR PROTEIN

The invention relates to a freeze-dried soft, flexible and continuous matrix of low-molecular weight hyaluronic acid or salt thereof containing at least one peptide or protein, useful as pharmaceutical composition.

Hyaluronic acid (HA) is a naturally occurring glycosaminoglycan consisting of a linear polymer of repeating units of glucuronic acid and N-acetyl-glucosamine. The molecular weight can vary over a wide range depending on the source. HA is present in several tissues of animals, and in some organs, such as rooster combs, in concentrations high enough for commercial scale extraction. Such tissue contains HA of a wide range of molecular weights and during a complex series of extraction, purification and sterilisation steps, high molecular weight chains are more or less degraded resulting in a final product having a considerably narrower molecular weight range. The critical parameters determining the characteristics of the final product in this respect are the molecular weight distribution of HA in the raw material, the degree of degradation of HA chains during the purification and sterilisation process and the effectiveness of removing low molecular weight HA.

A commercial available hyaluronic acid product is HEALON® (Kabi Pharmacia AB, Uppsala, Sweden) which has a average molecular weight of about 4 000 000 daltons. This product is produced as outlined in U.S. Pat No. 4,141,973 and is an ultrapure product. There are many literature references relating to the use of viscoelastic products of HA in ophthalmological application and the preparation of such products, including the preparation of chemically modified HA.

HA is known in slow release formulations and in WO 9005522 HA is mentioned as a slow release carrier together with a binding protein for e.g. GH or IGF.

In U.S. Pat. No. 4,772,419 a shaped article based upon cross-linked, possible derivatized HA or salt thereof, which is a substantially unswollen water-swellable state has a dry matter content of at least 65 percent by weight and a tensile strength greater than 100 N/cm$^2$ is disclosed. HA is of high molecular weight, i.e. about 3 000 000 Da. The article could be produced by freeze-drying. Thin sheets of paper-like structure or cellophane-like structures were obtained. The article could be used for preventing the adhesion and accretion of tissues.

Low molecular weight hyaluronic acid (LMWHA) could be produced by acid or enzymatic hydrolysation and thereafter fractionation. These processes are known in the art. LMWHA is known as carrier for pharmaceutical active agents and also for pharmaceutical activity itself.

In EP 138 572 a product comprising HA with Mw of 50 000–100 000 is stated as useful for wound healing and HA with a Mw of 500 000–730 000 is useful for intraocular and intra-articular injections. Fragments of HA as a carrier for drugs, e.g. EGF, in eyedrops is also disclosed. In EP 197 718 HA with different Mw between 30 000–730 000 is useful in the ophthalmic and dermatologic field. LMWHA with EGF is mentioned as example. HA with Mw of 500–800 000 together with water for cosmetic and skin disorder is known from GB 2 228 736. In U.S. Pat. No. 5,079,236 HA with Mw 50 000–200 000 for treatment of osteoarthritis and joint function is disclosed and in Jp 1 290 631 HA with Mw 50 000–3 000 000 for treatment of arthris, diabetic retinopathy is claimed. WO 9316732 and WO 9316733 disclose HA or fragments thereof (e.g. <750 000) and a drug e.g. anti-inflammatory NSAID, diclofenac, naproxen, anti-cancer, especially useful topically for skin.

In GB 2 235 204 is disclosed that a readily water-soluble film or sheet for cosmetic use is formed when hyaluronic acid is freeze-dried in vacuo. The hyaluronic acid used has a molecular weight of 1 200 000, giving a viscous solution in water. The layer containing magnesium-L-ascorbil phosphate is used as a cosmetic sheet for a face mask. Skin moisture, skin tension and whitening effect was shown for this composition.

EP 522 491 discloses a freeze-dried composition comprising hyaluronic acid and a polypeptide, which is administered by injection after reconstitution of the composition.

Our claimed composition comprises low molecular weight hyaluronic acid and peptide or protein, which gives unexpected advantageous effect when used for administration of a drug.

For the production of a matrix, which is soft, flexible and continuous and preferably in the form of a layer, special binding forces and interactions within the molecule are needed. Hyaluronic acid with a high molecular weight has a special structure of the molecule, which cannot be compared with the molecular structure of the low molecular weight hyaluronic acid. A person skilled in the art could not foreseen how the low molecular weight hyaluronic acid could react when freeze-dried.

When administrating a drug topically, a problem is to know how much drug is released during a certain time, so that the patient always receives the right dosage per time unit. When giving the drug dropwise on an ulcer, the total amount is well defined but there are difficulties in the administration of the drug in a defined amount over the whole surface and this method requires normally clinical care. When giving the drug in a paste-base, the exact amount of the drug is difficult to calculate and apply. Difficulties for sublingual or buccal composition can e.g. be stability problem due to a hydrophilic character of the base or calculation of the release time.

We have now found that when freeze-drying an aqueous solution of a peptide or protein and LMWHA which is not cross-linked, a layer in the form of a cake is formed with a structure like a wowen or a filter paper. The "paper" is porous, massive and homogenous. This "paper" can be cut in a desired form, can be torn and is easily handled. For this "paper" the exact amount of the drug per area is known. This means that the dosage can be accurate when the area of the "paper" is known. We have also found that when applying this "paper" topically, sublignally or buccally, the whole amount of the drug is quickly released. The drug is stable and keeps the activity within this formulation during storage. The claimed formulation is biocompatibile when applied on humans and is a perfect means for treatment of ulcers of different kind. The "paper" or "cake" can be applied directly to the ulcer or in the mouth. The drug will be thereby be quickly released by the pus or the saliva. We have also found that the drug can be present in a high concentration when freeze-dried together with low molecular weight HA.

The present invention relates thus to a freeze-dried soft, flexible and continuous matrix of low-molecular weight hyaluronic acid or salt thereof containing at least one peptide or protein. The molecular weight of the low-molecular weight hyaluronic acid is preferably between 50 000 and 200 000 Da. The invention also relates to pharmaceutical compositions in the form of a layer characterised by a freeze-dried low-molecular weight hyaluronic acid containing at least one peptide or protein. The drug could be e.g. GH, IGF-I, IGF-II or EGF or mixtures thereof. By GH is meant growth hormone or functional analogues thereof, by IGF is meant insulin-like growth factor or functional analogues thereof, both IGF-I and IGF-II and by EGF is meant epidermal growth factor or functional analogues thereof.

An antibiotic agent can be mixed with a growth hormone or growth factor when applied to a wound.

By functional analog is meant a substance having the same biological activity as the peptide or protein and having at least 65% homology with the peptide or protein.

The invention relates also to a process for the manufacture of the matrix or the pharmaceutical composition, which is characterised by freeze-drying a water solution of low-molecular weight hyaluronic acid and the peptide or protein in a layer. This freeze-drying and further production of the pharmaceutical article must be sterile.

The invention also relates to the use of freeze-dried low molecular weight hyaluronic acid in the form of a layer as carrier for peptide or protein This use is preferably for accurate dosing of the drug. The invention also relates to the use of the claimed pharmaceutical composition for the manufacture of a medicament for wound healing and to a method for accurately obtaining a predetermined dosage of a topically administerable peptide or protein which is characterised by freeze-drying a water solution of low-molecular weight hyaluronic acid and the peptide or protein to form a layer.

By low molecular weight is meant less than 1 000 000 D and preferably between 50 000 and 200 000 D. The layer can be between 1–40 mm and is preferably 2–12 mm. GH can be in a concentration of 1–200 IU/ml and is preferably 5–120 IU/ml. pH can be between 6.0 and 8.2 in the water solution prior to freeze-drying.

Growth hormone is here used as an example for the usefulness of the invention, but is not limiting the scope of protection by the claims.

Stability of Proteins

The stability of proteins depends on the chemical and physical properties of the protein. Different degradation pathways are known such as deamidation, oxidation, cleavage and aggregation.

Deamidation and oxidation are common chemical reactions comprising changes of the primary structure of the protein. Deamidation occurs especially in aqueous solutions but low temperature and low pH of the solutions suppress the deamidation reaction.

Different forms of aggregation result from the physical instability of the protein. Aggregates can be soluble or insoluble and binding of both the forms can be covalent or non covalent. The aggregates can give opalescent solutions but there can also be non-visible aggregation which only can be shown chemically. The prevention of covalent aggregation in protein formulations is of importance since such processes are irreversible and could result in the production of inactive species which in addition also may be immunogenic. Changes in the primary structure may also give rise to conformational changes which can be the cause of self association of the protein, aggregation. The non covalent aggregation occurring under certain conditions can lead to precipitation and loss of activity.

However, by monitoring these degradation reactions, it is possible to prove indirectly that the drug (in the examples GH) retains full biological activity. (Bristow A F et al. Pharmeuropa, Human Growth Hormone, Vol.3, 1–49, March 1991)

Methods

Isoelectric Focusing (IEF) With Densitometric Evaluation

IEF is a method according to which the extent of deamidation can be evaluated. The separation of hGH components is carried out in a pH gradient, which is established between two electrodes and stabilised by carrier ampholytes. The proteins migrate until they align themselves at their isoelectric point in the gradient, at which a protein possesses no net overall charge and will therefore concentrate as migration ceases. Thus the separation is obtained according to charge. The relative distribution of charged hGH forms are quantified by densitometric scanning of Coomassie Blue stained polypeptides. The higher percentage of the monomer, the less deamidation.

Polypeptides Size Distribution (SDS-PAGE)

Proteins in preparations of somatropin, hGH, were denatured by sodium dodecyl sulphate (SDS) to yield negatively charged molecular complexes of SDS-protein. Separation was then obtained according to molecular size by electrophoresis in polyacrylamide gels (PAGE) in the presence of SDS. The relative polypeptide size distribution of hGH was quantified by desitometric scanning of the silver stained polypeptide bands.

Visual Inspection

The appearance of the solutions were eye-inspected according to Ph. Eur. 2nd Ed. The scale is I to IV, and I is the most clear.

EXAMPLES

Example 1

Hyaluronic acid with a molecular weight of about 150 000 dalton has been produced from Na-hyaloronate. 2.51 g of Na-hyaloronate (Pharmacia AB, Sweden) was solved in 500 ml of water in argon atmosphere. 16 ml HCl was added and the mixture was thereafter stirred during 2 hours at 22–23° C. pH was <1. The solution was neutralised to pH 7.0 with 0.5 M NaOH. Thereafter 0.37 M HCl was added and the solution was stirred during 5 hours at 45° C. in argon atmosphere. pH 7.0 was then achieved with 0.5 M NaOH. The solution was dialysed by using a dialyse tube with distilled water. The used tube was 130885/10 30M with a cut off 12–14×$10^3$ D. The molecular weight of hyaluronic acid was analysed in the solution and the hyaluronic acid was freeze-dried. The freeze-drying was performed during 30 hours in a rotation freeze-drier at −5° C. to −50° C.

Example 2

Hyaluronic acid with a molecular weight (LMWHA) of 150 000 in water is mixed with growth hormone (GH, Genotropin® from Pharmacia AB, Sweden) so that each ml comprises 6.5 mg LMWHA and 110 IU GH. 10 ml of the solution is placed in a Petri dish with diameter of 70 mm with cover. The solutions are freeze-dried according to the following scheme:

Freezing:
   0–5° C. during 3 hours
   −45° C. during 26 hours
1st drying:
   −30° C. during 28 hours at 0.1 mBar
2nd drying
   +25° C. during 5–6 hours at 0.1 mBar After storage at 5–8° C. during one month the cake is dissolved in 2 ml distillated water and analyzed. The following results were obtained:

Table 1

TABLE 1

| Tests: | |
|---|---|
| 1. dissolving time (min) | 5 |
| 2. clarity | II |
| 3. SDS-PAGE | |
| aggregates (%) | 0.6 |
| GH (%) | 98.8 |
| Fragment (%) | 0.7 |
| 4. IEF | |
| Main component (%) | 99 |
| deamidation (%) | 0 |

Example 3

Hyaluronic acid with a molecular weight (LMWHA) of 150 000 is mixed with growth hormone (GH) (Genotropin® from Kabi Pharmacia AB, Sweden) in the following way: 65 mg hyaluronic acid was mixed with 2.65 ml of Genotropin®, 76 IU/ml. and diluted to 10 ml with destilled water, so that each ml comprises 6.5 mg LMWHA and 20.1 IU GH. 10 ml of the solution is dispensed in Petri dish with the diameter of 70 mm diameter with cover. The solutions are freeze-dried as described in Example 2. The freeze-dried cake is as a filter paper which can be bent and be cut. The diameter is 6.0 cm and the thickness is 0.5 cm. 1 cm² of the cake is formulated to contain 7.1 IU Genotropin® and 2.3 mg hyaluronic acid, 150 000 dalton.

1 cm² of the cake is cut out and analysed. See Table 2.

TABLE 2

| | Months | | |
|---|---|---|---|
| | 0 | 1 | 1 |
| Tests: | | 5° C. | 30° C. |
| 1. Dissolving time (min) | 1 | 2 | 3 |
| 2. SDS-PAGE | | | |
| aggregates (%) | 0.5 | 2.9 | 4.5 |
| GH (%) | 99 | 96.2 | 94.5 |
| Fragment (%) | 0.5 | 0.8 | 1.0 |
| 3. IEF | | | |
| Main component (%) | 99 | 97 | 94 |
| deamidation (%) | 1 | 1 | 0 |

The results for the claimed formulation confirms that a drug in a freeze-dried matrix of low-molecular weight hyaluronic acid can be stored in room temperature for at least one month in 30° C. This result was surprising, as proteins and especially GH normally are unstable and not possible to store in room temperature for such a long time.

By a biological assay, nephelometry, the amount of GH per area unit was determined. It was found that the growth hormone was uniformly (homogeneously) dispersed in the cake.

These results demonstrate indirectly that growth hormone retains full biological activity, since little or no degradation was observed after storage of growth hormone formulated with freeze-dried low molecular hyaluronic acid.

What is claimed is:

1. A pharmaceutical composition in the form of a layer comprising a freeze-dried, soft, flexible and continuous matrix of non-crosslinked hyaluronic acid having a molecular weight between 50,000 and 200,000 Da, or salt thereof, containing at least one peptide or protein.

2. A pharmaceutical composition in the form of a layer comprising a freeze-dried, soft, flexible and continuous matrix of non-crosslinked hyaluronic acid having a molecular weight between 50,000and 200,000 Da, or salt thereof, containing Growth Hormone (GH).

3. A process for the manufacture of a pharmaceutical composition according to claim 1, comprising freeze-drying a water solution of noncrosslinked hyaluronic acid having a molecular weight between 50,000 and 200,000 Da, or salt thereof, and at least one peptide or protein into a layer.

4. A pharmaceutical composition according to claim 1, wherein the at least one peptide or protein is selected from the group consisting of Growth Hormone (GH), Insulin-Like Growth Factor I (IGF-I), Insulin-Like Growth Factor II (IGF-II), Epidermal Growth Factor (EGF), and mixtures thereof.

5. A pharmaceutical composition according to claim 1, wherein the at least one peptide or protein comprises a mixture of an antibiotic agent and at least one member selected from the group consisting of Growth Hormone (GH), Insulin-Like Growth Factor I (IGF-I), Insulin-Like Growth Factor II (IGF-II), Epidermal Growth Factor (EGF), and mixtures thereof.

6. A pharmaceutical composition according to claim 2, comprising 1–200 IU/ml of Growth Hormone (GH).

7. A pharmaceutical composition according to claim 2, comprising 5–120 IU/ml of Growth Hormone (GH).

8. A pharmaceutical composition according to claim 2, wherein the layer has a thickness of from 1 to 40 mm.

9. A process according to claim 3, wherein the layer has a thickness of from 1 to 40 mm.

10. A process according to claim 3, wherein the water solution has a pH of from 6.0 to 8.2.

11. A method for wound healing, comprising applying a pharmaceutical composition according to claim 2 to a wound.

12. A method for providing a carrier for a peptide or protein, comprising freeze-drying in the form of a layer a noncrosslinked hyaluronic acid or salt thereof having a molecular weight between 50,000 and 200,000 Da and containing the peptide or protein.

13. A method for accurately dosing a peptide or protein, comprising dosing the pharmaceutical composition of claim 2.

14. A method for accurately preparing a pre-determined dosage of a topically administrable peptide or protein, comprising freeze-drying a water solution of noncrosslinked hyaluronic acid or salt thereof having a molecular weight between 50,000 and 200,000 Da and the peptide or protein to form a layer.

15. A pharmaceutical composition according to claim 1, wherein the layer has a thickness of from 1 to 40 mm.

16. A method for wound healing, comprising applying a pharmaceutical composition according to claim 1 to a wound.

17. A method for accurately dosing a peptide or protein, comprising dosing the pharmaceutical composition of claim 1.

18. A pharmaceutical composition in the form of a layer comprising a freeze-dried, soft, flexible and continuous matrix of non-crosslinked hyaluronic acid having a molecular weight between 50,000 and 200,000 Da, or salt thereof, containing at least one peptide selected from the group consisting of Insulin-Like Growth Factor I (IGF-I), Insulin-Like Growth Factor II (IGF-II), Epidermal Growth Factor (EGF), and mixtures thereof.

19. A pharmaceutical composition according to claim 18, wherein the layer has a thickness of from 1 to 40 mm.

20. A method for wound healing, comprising applying a pharmaceutical composition according to claim 18 to a wound.

21. A method for accurately dosing a peptide or protein, comprising dosing the pharmaceutical composition of claim 18.

* * * * *